(12) United States Patent
Lee

(10) Patent No.: US 8,034,386 B2
(45) Date of Patent: Oct. 11, 2011

(54) **EXTRACT FROM *AGARICUS BLAZEI* MURILL CAPABLE OF SUPPRESSING BREAST CANCER**

(75) Inventor: Insu Lee, Bethesda, MD (US)

(73) Assignees: SSI Co., Ltd., Tokyo (JP); Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 11/663,123

(22) PCT Filed: Sep. 12, 2005

(86) PCT No.: PCT/JP2005/016784
§ 371 (c)(1),
(2), (4) Date: Apr. 22, 2008

(87) PCT Pub. No.: WO2006/030750
PCT Pub. Date: Mar. 23, 2006

(65) Prior Publication Data
US 2008/0260772 A1    Oct. 23, 2008

(30) Foreign Application Priority Data
Sep. 17, 2004    (JP) ................................ 2004-272373

(51) Int. Cl.
*A01N 65/00*    (2009.01)
(52) U.S. Cl. ...................................................... 424/725
(58) Field of Classification Search .................. None
See application file for complete search history.

(56) References Cited

U.S. PATENT DOCUMENTS

| 6,093,694 A | 7/2000 | Fujimiya et al. |
| 2002/0004075 A1* | 1/2002 | Yigzaw ......................... 424/725 |
| 2007/0184066 A1* | 8/2007 | Lee et al. ................. 424/195.15 |

FOREIGN PATENT DOCUMENTS

| JP | 2000-159682 | 6/2000 |
| JP | 2004-210768 | 7/2004 |
| WO | WO 98/27992 A1 | 7/1998 |
| WO | WO 02/15917 A1 | 2/2002 |
| WO | WO 03/051382 A1 | 6/2003 |
| WO | WO 2004/004748 | * 1/2004 |

OTHER PUBLICATIONS

Narita et al., 17(2):31-42 (1998) (with English summary).

* cited by examiner

*Primary Examiner* — Michael Meller
(74) *Attorney, Agent, or Firm* — King & Spalding LLP; Peter J. Dehlinger; Susan J. Myers Fitch

(57) ABSTRACT

A food material capable of suppressing the genesis of breast cancer or proliferation of terminal breast cancer. An extract of *Agaricus Blazei* Murill comprising an ingredient capable of suppressing the genesis of breast cancer or proliferation of terminal breast cancer is provided. This ingredient can be a chromatographic main elution fraction of 100 to 2000 molecular weight obtained through the steps of extracting the fruit body of *Agaricus Blazei* Murill with hot water, dialyzing the obtained extract and subjecting the obtained dialysis external fluid to chromatography. Alternatively, the above ingredient can be a dialysis external fluid obtained through the steps of extracting the fruit body of *Agaricus Blazei* Murill with hot water, adding ethanol to the obtained extract to thereby obtain precipitates, and dissolving the precipitates in water and dialyzing the resultant solution.

8 Claims, 6 Drawing Sheets

EXTRACT FROM *AGARICUS BLAZEI* MURILL CAPABLE OF SUPPRESSING BREAST CANCER

The present application is a national stage entry under 35 U.S.C. §371 of PCT Application No. PCT/JP2005/016784, filed Sep. 12, 2005, now pending, which claims priority to Japanese Application No. 2004-272373, filed Sep. 17, 2004, now pending, both of which are incorporated by reference herein.

TECHNICAL FIELD

The present invention relates to an extract of *Agaricus Blazei* Murill, which suppresses breast cancer. More specifically, the present invention relates to an extract of *Agaricus Blazei* Murill, which contains an ingredient capable of suppressing the genesis of breast cancer or proliferation of terminal breast cancer. Even more specifically, the present invention relates to an extract of *Agaricus Blazei* Murill, which suppresses the proliferation of breast cancer induced by methyl-N-nitrosourea.

BACKGROUND ART

The Mushroom, which is generally called Kawariharatake, belongs to the family Agaricaceae of the division Basidiomycota, and is referred to by the botanical name "*Agaricus blazei* Murill" and the Japanese name "Kawariharatake". *Agaricus blazei* Murill (hereinafter, generally referred to as Kawariharatake, ABM, or *agaricus*) has been traditionally used as a medicament in the Piedade region in Sao Paulo, Brazil. It is said that Kawariharatake has a variety of immunostimulatory activities and effects on cancer prevention and suppression of tumor growth. Currently, it is widely provided for internal use as health food.

Polysaccharides contained in Kawariharatake include β-1,6-glucopyranosyl residues and have anti-tumor activity against Sarcoma 180 (Ebina T et al. (1986), Jpn. J. Cancer Res 77:1034-1042).

Extracts from Kawariharatake include (1→4)-α-D-glucan having (1→6)-β branched chain, and they have natural killer cell activation activity and selective anti-tumor activity mediated through apoptosis (Fujimiya Y et al. (1998), Cancer Immunol Immunother 46:147-159).

Peptideglycans from Kawariharatake have a direct cytotoxic activity against Meth A tumor cells in a double implanted tumor system and an indirect immune enhancement activity in tumor-bearing mice (Ebina T et al. (1998), Biotherapy 11:259-265).

Polysaccharides contained in Kawariharatake changed the percentage of spleen Thy1,2-, L3T4 positive cells in a T cell subset of mice (Mizuno M et al. (1998), Biosci. Biotechnol. Biochem. 62:434-437).

These reports suggest that polysaccharides contained in Kawariharatake have cytotoxic activity against tumor cells through an immunomodulation activity.

In this manner, although there are many reports regarding immune enhancing activities and anti-cancer activities of Kawariharatake extract, those tests were conducted in vitro or conducted on animals already suffering from cancer to examine the effects of Kawariharatake, and none of those examined the effects of Kawariharatake in the genesis of cancer such as breast cancer. Further, there are no reports, to the best of inventor's knowledge, that examined the effects of Kawariharatake extract and ingredients contained therein on terminal cancer.

Non-patent document 1: Ebina T et al. (1986), Jpn. J. Cancer Res 77:1034-1042
Non-patent document 2: Fujimiya Y et al. (1998), Cancer Immunol Immunother 46:147-159
Non-patent document 3: Ebina T et al. (1998), Biotherapy 11:259-265
Non-patent document 4: Mizuno M et al. (1998), Biosci. Biotechnol. Biochem. 62:434-437.

DISCLOSURE OF THE INVENTION

Problems to be Solved by the Invention

Breast cancer is one of the major diseases in females. The present invention aims to provide drug materials and food materials which can suppress breast cancer. The present invention aims to provide drug materials and food materials which suppress the genesis of breast cancer and proliferation of terminal breast cancer.

Means for Solving the Problems

The present invention relates to Kawariharatake extract comprising an ingredient which suppresses breast cancer.

The present invention also relates to Kawariharatake extract comprising an ingredient which suppresses genesis of breast cancer and proliferation of terminal breast cancer.

Preferably, the extract is prepared by conducting extraction with a solvent.

Preferably, the extract is prepared by conducting extraction with hot water.

Preferably, the ingredient is a chromatographic main elute fraction of 100 to 2000 molecular weight obtained by the steps of extracting the fruit body of Kawariharatake with hot water, dialyzing the resultant extract, and subjecting the thus obtained dialysis external fluid to chromatography.

Preferably, the ingredient is a dialysis external fluid obtained by the steps of extracting the fruit body of Kawariharatake with hot water, adding ethanol to the resultant extract, thereby obtaining precipitates, followed by dissolving the precipitates in water, and dialyzing the solution.

Typically, the above-mentioned breast cancer is induced by methyl-N-nitrosourea.

The present invention also relates to a composition for suppressing breast cancer, which comprises an Kawariharatake extract, and a pharmaceutically acceptable carrier.

Typically, the above-mentioned composition is in a form selected from the group consisting of powder, liquid, tablet, capsule and pellet.

The present invention also relates to a method for suppressing breast cancer. The method comprises the step of administering the composition to a subject, which comprises an Kawariharatake extract, and a pharmaceutically acceptable carrier.

The present invention also relates to a method for suppressing genesis of breast cancer or proliferation of terminal breast cancer, comprising the step of administering to a subject, the composition comprising an Kawariharatake extract, and a pharmaceutically acceptable carrier.

Preferably, the above-mentioned extract is a chromatographic main elute fraction of 100 to 2000 molecular weight obtained by the steps of extracting the fruit body of Kawariharatake with hot water, dialyzing the resultant extract, and subjecting the thus obtained dialysis external fluid to chromatography.

Preferably, the above-mentioned extract is a dialysis external fluid obtained by the steps of extracting the fruit body of Kawariharatake with hot water, adding ethanol to the resultant extract, thereby obtaining precipitates, followed by dissolving the precipitates in water, and dialyzing the resultant solution.

The present invention also relates to the use of Kawariharatake extract for preparing a composition for suppressing breast cancer.

The present invention also relates to the use of Kawariharatake extract for preparing a composition for suppressing genesis of breast cancer or proliferation of terminal breast cancer.

Preferably, the above-mentioned extract is a chromatographic main elute fraction of 100 to 2000 molecular weight obtained by the steps of extracting the fruit body of Kawariharatake with hot water, dialyzing the resultant extract, and subjecting the thus obtained dialysis external fluid to chromatography.

Preferably, the above-mentioned extract is a dialysis external fluid obtained by the steps of extracting the fruit body of Kawariharatake with hot water, adding ethanol to the resultant extract, thereby obtaining precipitates, followed by dissolving the precipitates in water, and dialyzing the resultant solution.

Effects of the Invention

Kawariharatake extract includes an ingredient which suppresses breast cancer. Kawariharatake extract includes an ingredient which suppresses genesis of breast cancer or proliferation of terminal breast cancer. Since this ingredient suppresses the stage in which cancer (especially breast cancer) is induced and proliferation of induced cancer in terminal stage, a drug material and a food material which are effective in suppressing breast cancer can be provided.

BEST MODE FOR CARRYING OUT THE INVENTION

Figure 1:
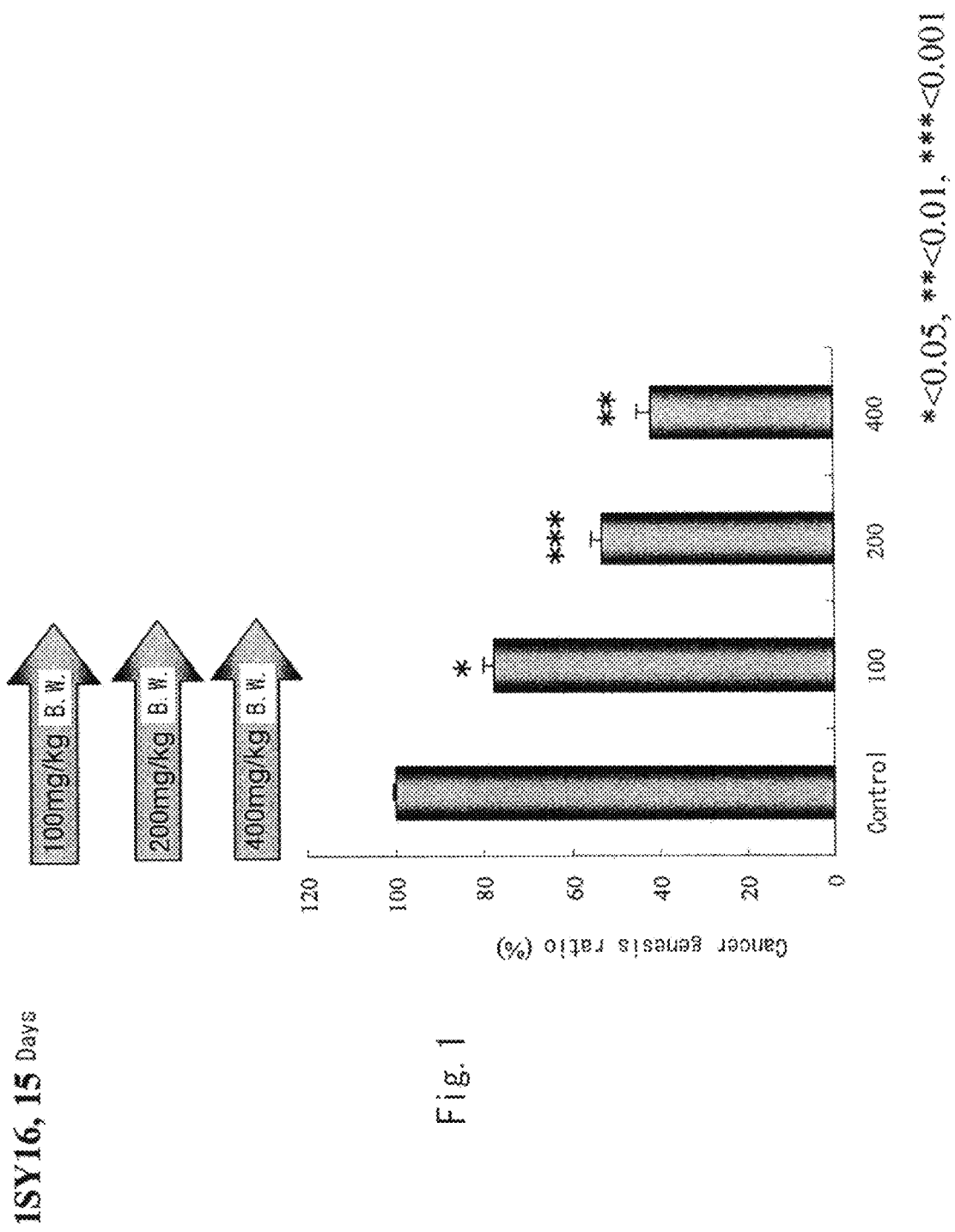
FIG. 1 shows effects of Kawariharatake extract (1SY16) of the present invention which suppresses genesis of breast cancer.

As used herein, the term "Kawariharatake" generally means Kawariharatake material including the fruit body, mycelium, and culture of the Mushroom which belongs to the family Agaricaceae of the division Basidiomycota, and is referred to by the botanical name "*Agaricus blazei* Murill" and the Japanese name "Kawariharatake". The term "Kawariharatake" typically means fruit body of Kawariharatake. Hereinafter, "Kawariharatake", "AMB", and "*Agaricus*" are used interchangeably, and used to mean the same Kawariharatake material.

Kawariharatake extract of the present invention is prepared by extracting Kawariharatake material with a solvent. Typically, Kawariharatake material is a fruit body of natural or cultivated Kawariharatake. Mycelium of Kawariharatake cultivated in a culturing tank, or the like can be used. Normally, Kawariharatake is used after washing followed by drying. Commercially available dried fruit body is also used conveniently. Normally, dried Kawariharatake is powdered according to a conventional method, and used as a starting material for extraction.

The Kawariharatake extract of the present invention can be obtained by conducting an extraction procedure after adding various solvents to the dried fruit body or a powder thereof. In general, a solvent 2 to 10 times the weight of the dried fruit body, or the powder thereof is added to carry out extraction. As the above solvent, water, ethanol, propanol, butanol, acetone, 1,3-butylene glycol, ethyl acetate, hexane, methylene chloride, methanol, or a mixture thereof is used. Typically, water is used to prepare an Kawariharatake extract.

Extraction procedure can be conducted by mixing or shaking the mixture of Kawariharatake powder and any of the above solvent using a magnetic stirrer (at the rotating number of 100 to 500 rpm), or the like, at a temperature of 0° C. to 100° C., preferably room temperature to 80° C., for 10 minutes to several days, preferably 1 to 24 hours. Typically, Kawariharatake extract of the present invention can be obtained by adding deionized water to Kawariharatake powder, and continuously mixing for 24 hours at 70° C. From thus obtained solution, dry material is obtained by lyophilization, or the like after removing residues according to conventional methods such as centrifugation, filtration, and the like. Thus obtained dry material, or the like is referred to as Kawariharatake extract.

An ingredient, which suppresses genesis of breast cancer and even proliferation of terminal breast cancer, contained in thus obtained Kawariharatake extract can be obtained by procedures known to the skilled artisan such as high performance liquid chromatography (HPLC). The structure of the obtained ingredient can be identified using a technique such as nuclear magnetic resonance (NMR) method, and the like.

The following is one example of the method for manufacturing Kawariharatake extract.

Water of 5 to 10 times the weight of the dried fruit body, is added to the fruit body Kawariharatake, followed by heat-extracting or heat-refluxing the mixture for 1 to 3 hours preferably at a temperature of 95° C. or above. As required, this hot water extraction from Kawariharatake can be carried out repeatedly using a residue previously extracted with hot water. The solution extracted with hot water thus obtained is dried by a method known to the skilled artisan such as lyophilization, spray-drying, or the like to obtain a dried product (hereinafter, referred to as dried product A). This dried product A is mixed with water of 5 to 20 times the volume of product A. Then, the solution is poured into a dialysis tube and dialyzed for 10 to 15 hours with distilled water of several times the volume of product A. The obtained dialysate is lyophilized to obtain a dried product (hereinafter, referred to as dried product C) which contains an ingredient suppressing genesis of breast cancer and even proliferation of terminal breast cancer.

Then, the solution remaining in the dialysis tube is further dialyzed with running water for 20 to 40 hours dialyzed twice with distilled water for a few hours each time and a dried product of the solution remaining in the dialysis tube is obtained as described above. Thus, the dried product (hereinafter, referred to as dried product B), which also contains an ingredient suppressing genesis of breast cancer and even proliferation of terminal breast cancer, can be obtained.

Next, the above obtained dried product C is dissolved in distilled water of about ten times the weight of product C. Gel filtration chromatography is carried out using distilled water as an eluent to obtain a number of fractions by fractionating 20 mL each. Among the obtained fractions, a fraction or fractions in the middle of the elution peak, which has a molecular weight of about 100-2000 Da by gel filtration, is preferably used as an ingredient suppressing genesis of breast cancer and even proliferation of terminal breast cancer.

These fractions are analyzed further using reverse-phase chromatography, which uses ODS (octadecyl silanated silica gel), ion-exchange chromatography using DEAE-TOYOPEARL 650, or the like, and confirmed to include a plurality of ingredients besides arginine, lysine, mannitol, and the like.

The solution extracted with hot water, obtained by the above-described method, is mixed with an equal amount of ethanol. The mixture is centrifuged to separate a precipitate from a supernatant. The obtained supernatant is further mixed with ethanol of 1 to 3 the volume of the supernatant. The mixture is further centrifuged to obtain a precipitate. The precipitate obtained is dissolved in distilled water and the solution obtained, is dialyzed. The dialysate obtained is also an ingredient suppressing genesis of breast cancer and even proliferation of terminal breast cancer of the present invention.

The thus obtained Kawariharatake extract or an ingredient contained therein suppressing genesis of breast cancer and even proliferation of terminal breast cancer can be used in manufacturing pharmaceutical formulations, as it is, or along with various carriers.

Typically, the thus obtained Kawariharatake extract or an ingredient contained therein, which suppresses genesis of breast cancer and even proliferation of terminal breast cancer, can be formulated as a composition which can be ingested orally along with a pharmaceutical carrier which is compatible with the living body (For example, saline, buffered physiological saline, dextrose, and water, or the like).

The above described pharmaceutically acceptable carriers are known to those skilled in the art and include, for example, the following carriers but are not limited to these: buffers such as Ringer's solution, Hank's balanced salt solution, and buffered physiological saline; fatty acids such as sesame oil; synthetic fatty acid esters such as ethyl oleate and triglycerides; saccharides such as lactose, sucrose, mannitol, sorbitol; starches derived from plants such as corn, wheat, rice, and potato; cellulose such as methylcellulose, hydroxypropylmethylcellulose, and sodium carboxymethylcellulose; rubber such as gum arabic or tragacanth; proteins such as gelatin and collagen; cross-linked polyvinyl pyrrolidone, agar, alginic acid or salts thereof, or the like.

The thus obtained Kawariharatake extract or an ingredient contained therein which suppresses genesis of breast cancer and even proliferation of terminal breast cancer, prepared as described above, can be ingested alone or in combination with other drugs or food materials.

The thus obtained Kawariharatake extract or an ingredient contained therein which suppresses genesis of breast cancer and even proliferation of terminal breast cancer and composition thereof, prepared as described above, can be administered orally or parenterally. Parenteral administration is accomplished via intravenous, intramuscular, intraperitoneal or intranasal administration. The details of formulation and administration of the pharmaceutical composition according to the present invention can be performed in accordance with descriptions in a textbook in the field of art, for example, "REMINGTON'S PHARMACEUTICAL SCIENCES" (Maack Publishing Co., Easton, Pa.).

Kawariharatake extract or an ingredient contained therein which suppresses genesis of breast cancer and even proliferation of terminal breast cancer for oral administration can be formulated as a composition including a pharmaceutically acceptable carrier well known in the art, in an administration form suitable for ingestion. Such a carrier allows the composition obtained to be formulated as a tablet, pill, sugar-coated pill, capsule, liquid, gel, syrup, slurry, suspension, or the like, suitable for ingestion by patients.

The composition of the present invention includes hot water extract of Kawariharatake or an ingredient contained therein which suppresses genesis of breast cancer and even proliferation of terminal breast cancer in an amount effective for suppressing genesis of breast cancer and even proliferation of terminal breast cancer. The skilled artisan will thoroughly understand and recognize the "pharmaceutically effective amount for suppressing genesis of breast cancer and even proliferation of terminal breast cancer". The "pharmaceutically effective amount for suppressing genesis of breast cancer and even proliferation of terminal breast cancer" can be evaluated in vitro assay using a cell culture or an appropriate animal model. Next, an effective amount for ingestion in human can be determined from such information obtained from the above evaluation. The "pharmaceutically effective amount for suppressing genesis of breast cancer and even proliferation of terminal breast cancer" can be determined by, for example, using an assay system using Sprague-Dawley Rat in which breast cancer is induced by administrating carcinogen, methyl-N-nitrosourea, as described herein.

The amount of Kawariharatake extract, which is actually ingested, depends on the health condition, or the like of the individual to be administered, and can be optimized to attain the desired effects. It is a routine procedure for the skilled artisan to decide a pharmaceutically or nutritionally effective amount thereof.

The above described Kawariharatake extract or an ingredient contained therein which suppresses genesis of breast cancer and even proliferation of terminal breast cancer can be mixed with one or more selected food materials in an amount sufficient for exerting its function. The one or more selected food materials are mixed with the above described Kawariharatake extract or the ingredient which suppresses genesis of breast cancer and even proliferation of terminal breast cancer in a form known to the skilled artisan, usually, in powder form. The mixture can be served as a liquid food product depending on its utility or preference. Alternatively, the mixture may be prepared in the form of capsules such as hard capsules or soft capsules, tablets or pills, or may be made into a powdery, granular, tea-leaf, tea-bag, or candy form.

The above described Kawariharatake extract or an ingredient contained therein which suppresses genesis of breast cancer and even proliferation of terminal breast cancer suppresses genesis of breast cancer and proliferation of the generated breast cancer induced by methyl-N-nitrosourea. The present invention is based on the study concerning the therapy on the carcinogen using Kawariharatake extract in various forms of administration formulation. By referring to the procedure or protocol disclosed herein, the effectiveness of the above described Kawariharatake extract or an ingredient suppressing genesis of breast cancer and even proliferation of terminal breast cancer on the other cancer induced by the other carcinogens can be demonstrated easily.

That is, it can be easily demonstrated by changing the concentration of the above described Kawariharatake extract or an ingredient which suppresses genesis of breast cancer and even proliferation of terminal breast cancer in feed and measuring the level of suppression of genesis of cancer and proliferation of induced cancer in mice which are administered with a carcinogen.

Hereinafter, the present invention will be further described by way of examples in which methyl-N-nitrosourea is used as a carcinogen. The following examples are merely illustrative and do not limit the present invention.

Hereinafter, the present invention will be explained by examples.

Example 1

Preparation of Kawariharatake Extract (1) The above described dried product A was used as a Kawariharatake hot water extract. This was obtained by extracting a dried fruit body of Kawariharatake (Kyowa's *Agaricus* Mushroom) with boiling water, removing the residue by centrifugation, at 1800×g, for 10 minutes followed by lyophilization. This was dissolved in purified water at a concentration of 3.7 mg/ml to form Sample I, and at a concentration of 8 mg/ml to form Sample II.

(2) Distilled water (2 L) was added to 300 g of Kyowa's *Agaricus* Mushroom, and the mixture was heat refluxed at 95° C. or higher for two hours. The solution obtained was filtered to separate the filtrate (a solution extracted with hot water) and the residue. Again, 2 L of distilled water was added to the residue and the mixture was heat refluxed at 95° C. or higher for another two hours to perform hot water extraction and a filtrate was obtained. Further, the same procedure was repeated once more with regard to the remaining residue. The filtrates obtained were lyophilized together to obtain dried product A (153 g: extraction rate of 51%).

Distilled water (500 mL) was added to 50 g of dried product A and the mixture was poured into a dialysis tube (Spectra/Por Membrane 50×31, inner diameter of 8 mm and length of 30 cm, FE-0526-65). The mixture was dialyzed with 3 L of distilled water for 12 hours. The dialysis ethanol fluid was lyophilized to obtain dried product C (27 g: extraction rate of 53%). The remaining solution in the dialysis tube was further dialyzed with running water for 30 hours, and then dialyzed twice with distilled water (four hours each time, 8 hours in total). Thereafter, the dialysis internal fluid was lyophilized to obtain dried product B (11 g: extraction rate of 22%). Subsequently, 3 g of dried product C was dissolved in 30 mL of distilled water and chromatography using TOYOPEARL HW40C (inner diameter of 40 mm and length of 420 mm) was performed. The eluent was entirely distilled water. For each fraction, 20 ml of the aliquots were taken to obtain fractions 1 to 30. These fractions were divided into the following five groups with reference to results of thin-layer chromatography analysis. The dried weights were as follows: fractions 1 to 11 (75 mg, 2.5%); fractions 12 to 15 (920 mg, 30.7%); fractions 16 to 17 (1570 mg, 52.3%); fractions 18 to 19 (270 mg, 9%); and fractions 20 to 28 (97 mg, 3.2%).

Infrared radiation (IR) absorption spectrum data of fraction 16 (hereinafter, sometimes referred to as 1SY-16) was as follows.
Fraction 16: IR (KBr) 3390, 3325, 3285, 2940, 2920, 1641, 1634, 1622, 1615, 1600, 1595, 1405, 1394, 1084, 1020: molecular weight (estimated by gel filtration) 100-2000 Da (3) Hot water extraction similar to that described in above (2) was carried out to obtain 6 L of a combined filtrate (a solution extracted with hot water). The filtrate was concentrated under reduced pressure to 1 L, and 1 L of ethanol was added thereto and mixed, followed by centrifugation to obtain precipitate and supernatant. Ethanol (3 L) was further added to the supernatant and mixed, and the mixture was centrifuged to obtain a precipitate, and the precipitate was dissolved in distilled water and dialyzed. The external dialysate obtained was lyophilized to obtain a powder (hereinafter sometimes referred to as ABMK-22).

Example 2

Prevention of Breast Cancer Induced by MNU by Kawariharatake Extract

Effects of preventing breast cancer by Kawariharatake extract (1SY16 and ABMK22) were evaluated using rat breast cancer model in which breast cancer is induced by methyl-N-nitrosourea (MNU: breast cancer inducing material).

Sprague-Dawley rat (female, 50 days old) was used. Rats were fed with Standard 4% Teklad Rat Feed purchased from Hyland Feed Nutrition Company (Madison, Wis.). Breast cancer was induced by one intravenous injection of MNU, which was dissolved in distilled water and adjusted to pH 5.0, with a dose of 50 mg/kg body weight.

At two hours after MNU injection, Kawariharatake extract (1SY16 or ABMK22) was administered to rats with induced breast cancer, which were divided into groups (group 1 to 4) as described below, and the test in which rats were bred for five months in total was conducted.

In group 1, the rats were divided into four groups with each group consisting of five rats. Rats in each group were administered orally (gavage) with 1SY16 for two weeks, while changing the concentration thereof to be 0 mg/kg body weight (control group), 100 mg/kg body weight, 200 mg/kg body weight and 400 mg/kg body weight per day, respectively. Hereinafter, this gavage method is referred to as oral administration.

In group 2, the rats were divided into four groups with each group consisting of five rats. Rats in each group were administered orally with 1SY16 of 200 mg/kg body weight/day. Rats in group 1 were administered with 1SY16 for 1 to 15 days after MNU intravenous injection. Rats in group 2 were administered with 1SY16 for 31 to 60 days after MNU intravenous injection. Rats in group 3 were administered with 1SY16 for 61 to 90 days after MNU intravenous injection. Rats in group 4 were administered with 1SY16 for 91 to 120 days after MNU intravenous injection. Rats in group 5 were administered with drinking water as a control.

In group 3, rats were divided into five groups with each group consisting of five rats. Rats in group 1 were administered with drinking water as a control. Rats in groups 2 to 5 were administered for 120 days with different dosages of Kawariharatake extract (ABMK22), namely 50 mg/kg body weight, 100 mg/kg body weight, 200 mg/kg body weight and 400 mg/kg body weight, per day, respectively.

In group 4, rats were divided into five groups with each group consisting of five rats. Rats in group 1 were administered with drinking water as a control. Rats in groups 2 to 5 were administered over different period of time and different dosages of Kawariharatake extract (ABMK22), namely with 400 mg/kg body weight (during 1 to 120 days), 800 mg/kg body weight (during 31 to 60 days), 1600 mg/kg body weight (during 61 to 90 days) and 3200 mg/kg body weight (during 91 to 120 days), per day, respectively.

After the experimental duration of five months, rats were sacrificed, and the number of breast cancer occurrence in rats of each group, and the weight of the breast cancer developed were each measured.

Results are indicated in FIG. 1 to FIG. 6.

FIG. 1 indicates the result of tests in group 1. The horizontal axis of FIG. 1 indicates, from left, control group, group administered with 100 mg/body weight of 1SY16, group administered with 200 mg/body weight of 1SY16 and group administered with 400 mg/body weight of 1SY16, respectively. The vertical axis of FIG. 1 indicates the occurrence ratio of breast cancer in each group relative to that of the control group, with the control group being 100%. The arrows in the upper panel illustrate oral administration of 1SY16 for two weeks.

As indicated in FIG. 1, 1SY16 decreased the occurrence of breast cancer depending on dosage by about 22% in 100 mg/body weight administration group, about 43% in 200 mg/body weight administration group and about 55% in 400 mg/body weight administration group.

In FIG. 1, * indicates a statistically significant difference with $p<0.05$ when compared to the occurrence ratio of the control group,  indicates that with $p<0.01$, and * indicates that with $p<0.001$, respectively.

Figure 2:
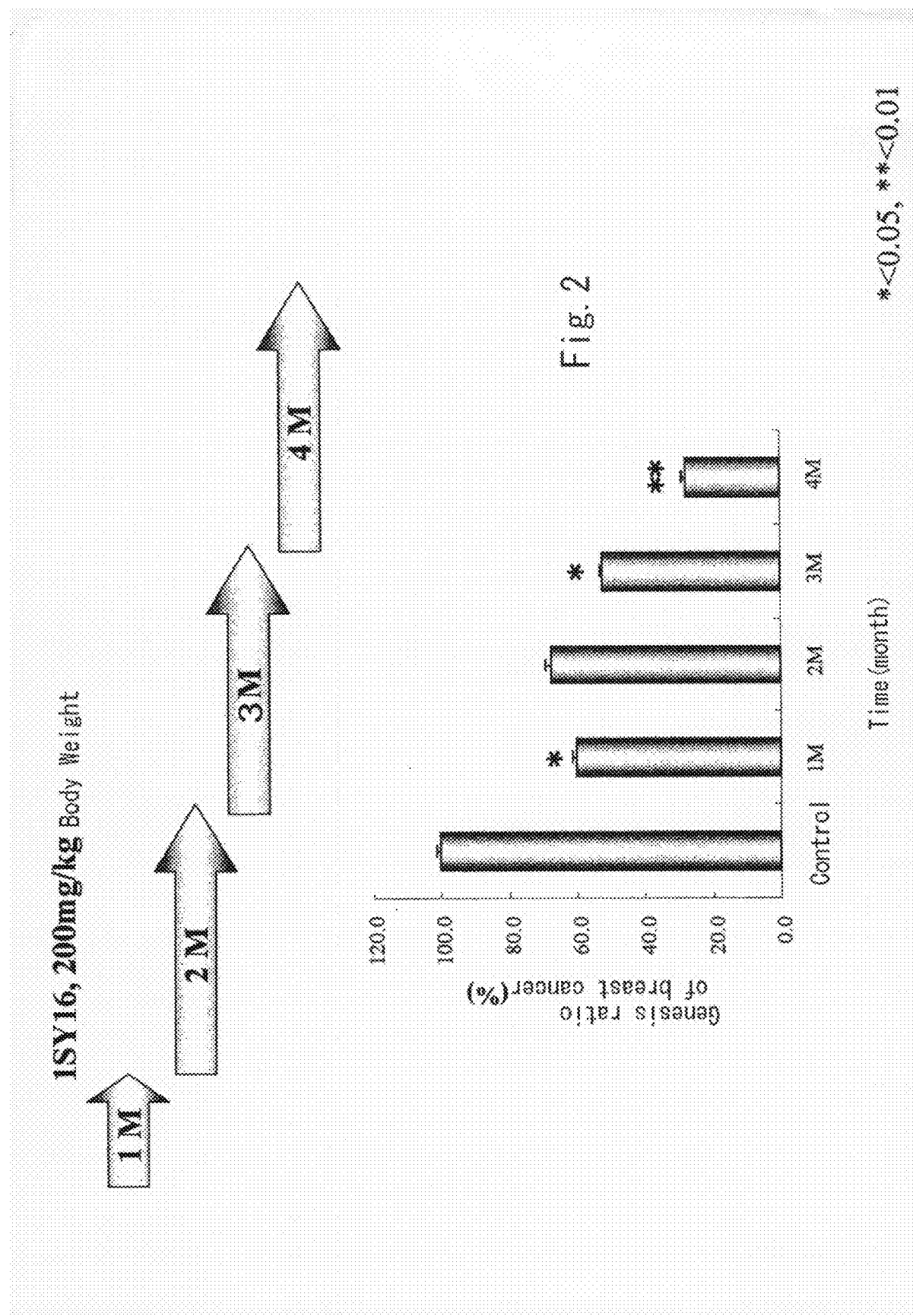
FIG. 2 shows effects of Kawariharatake extract (1SY16) of the present invention which suppresses genesis of breast cancer.

FIG. 2 indicates the result of tests in group 2. The horizontal axis of FIG. 2 indicates, from left, groups of durations of 1SY16 oral administration, 1 to 15 days, 31 to 60 days, 61 to 90 days, and 91 to 120 days, respectively. The group in which rats were administered with 1SY16 after MNU intravenous injection for 1 to 15 days is represented by 1M (one month), the group for 31 to 60 days is represented by 2M (two months), the group for 61 to 90 days is represented by 3M (three months), and the group for 91 to 120 days is expressed as 4M (four months), respectively. The arrows in the upper panel illustrate administration duration of 1SY16. The vertical axis of FIG. 2 indicates the occurrence ratio of breast cancer in each group, relative to that of the control group, with the control group being 100%, similar to FIG. 1.

As indicated in FIG. 2, 1SY16 decreased the occurrence of breast cancer, depending on the administration duration, by about 40% in one month administered group, about 35% in two months administered group, about 46% in three months administered group and about 72% in four months administered group. * and ** in FIG. 2 indicate statistically significant differences relative to a control group, similar to that in FIG. 1.

Figure 3:
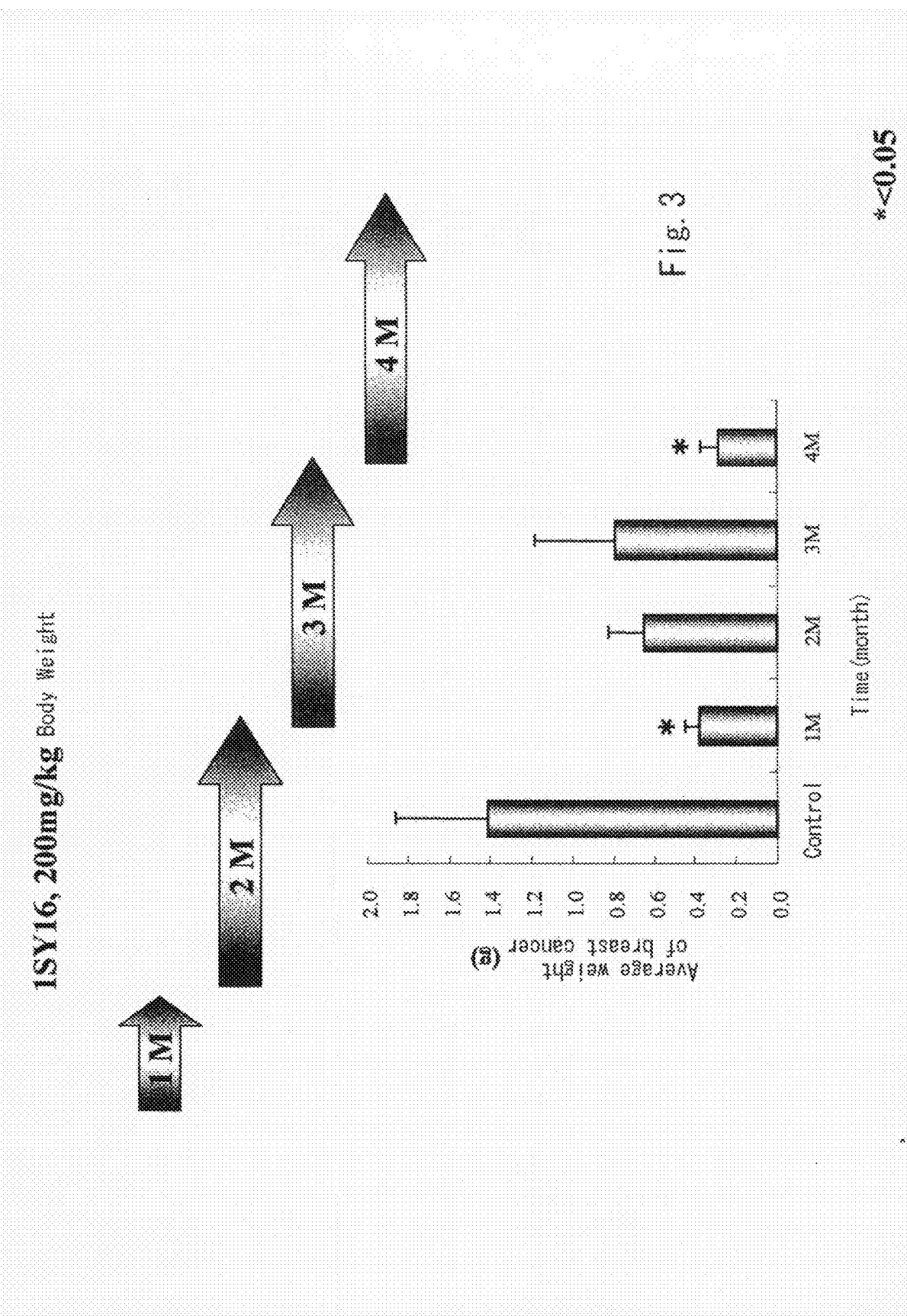
FIG. 3 shows effects of Kawariharatake extract (1SY16) of the present invention which suppresses proliferation of breast cancer.

FIG. 3 indicates the average weight of breast cancer in each group in the test indicated in FIG. 2. As being apparent from FIG. 3, the average weight of breast cancer in each group is about 26%, 46%, 54% or 17%, as compared to that of a control group, respectively, and decreases generally depending on the period of administration, similar to occurrence ratio of breast cancer. * in FIG. 3 indicates a statistically significant differences relative to a control group, similar to those in FIGS. 1 and 2.

Based on the results indicated in FIG. 2 and FIG. 3, it was indicated that not only genesis of breast cancer but also proliferation of generated breast cancer, especially terminal breast cancer is suppressed. Further, based on the results indicated in FIG. 2 and FIG. 3, suppressive effects were confirmed even in the administration during 91 to 120 days after induction of breast cancer, and thus significant proliferation suppressive effects compared to a control group were also confirmed.

Figure 4:
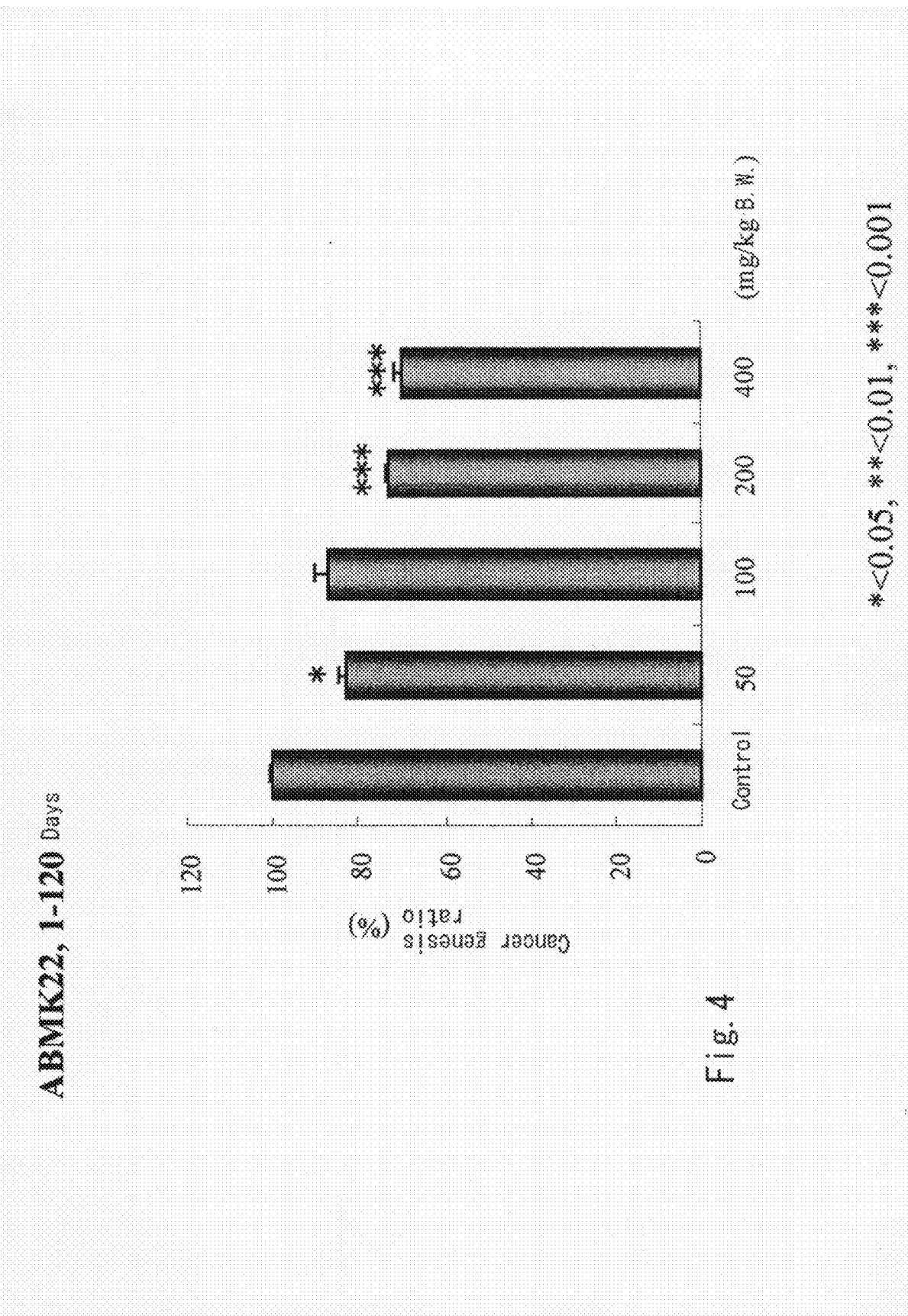
FIG. 4 shows effects of Kawariharatake extract (ABMK22) of the present invention which suppresses genesis of breast cancer.

FIG. 4 indicates the result of tests in group 3. The horizontal axis of FIG. 4 indicates, from left, control group, group administered with 50 mg/kg bodyweight of ABMK22, group administered with 100 mg/kg body weight of ABMK22, group administered with 200 mg/kg body weight of ABMK22, and group administered with 400 mg/kg body weight, respectively. The vertical axis of FIG. 4 indicates the occurrence ratio of breast cancer in each group, relative to that of the control group, with the control group being 100%, similar to FIGS. 1 and 2.

As indicated in FIG. 4, in ABMK22 administration groups, the occurrence of breast cancer decreased depending on the dosage thereof with about 82% in the group administered with 50 mg/kg body weight compared to that of the control group, about 85% in the group administered with 100 mg/kg body weight compared to that of the control group, about 73% in the group administered with 200 mg/kg body weight compared to that of the control group, and about 70% in the group administered with 400 mg/kg body weight compared to that of the control group, thus showing that the occurrence of breast cancer is suppressed. When these results are expressed in an inhibitory ratio, those in the above described groups are about 18%, about 15%, about 27% and about 30%, respectively. *,  and * in FIG. 4 indicate statistically significant differences relative to a control group, similar to those in FIGS. 1 to 3.

Figure 5:
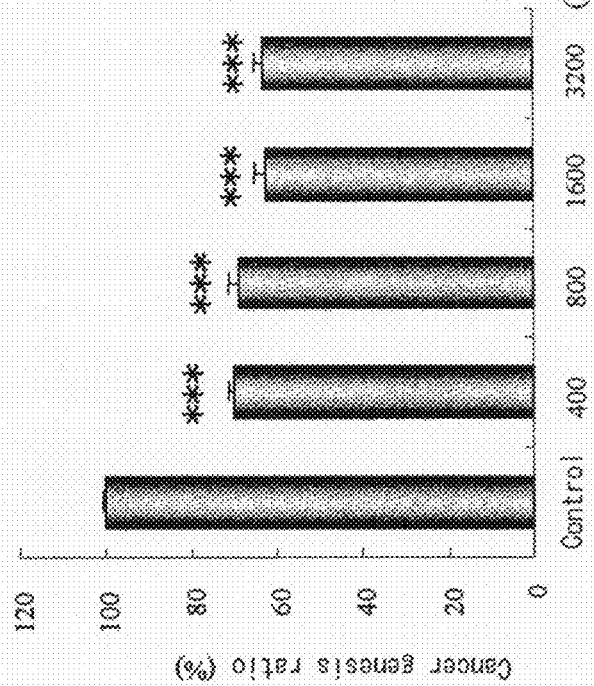
FIG. 5 shows effects of Kawariharatake extract (ABMK22) of the present invention which suppresses genesis of breast cancer.

FIG. 5 indicates the result of tests in group 4. The horizontal axis of FIG. 5 indicates, from left, control group, group administered with 400 mg/kg body weight of ABMK22, group administered with 800 mg/kg body weight of ABMK22, group administered with 1600 mg/kg body weight of ABMK22, and group administered with 3200 mg/kg body weight of ABMK22, respectively. The vertical axis of FIG. 5 indicates the occurrence ratio of breast cancer in each group, relative to that of the control group, with the control group being 100%, similar to those in FIGS. 1, 2 and 4. The arrows in FIG. 5 illustrate ABMK22 administration duration.

As indicated in FIG. 5, in ABMK22 administered groups, the occurrence of breast cancer decreased depending on the dosage thereof with about 68% in the group administered with 400 mg/kg body weight compared to that of the control group, about 66% in the group administered with 800 mg/kg body weight compared to that of the control group, about 62% in the group administered with 1600 mg/kg body weight compared to that of the control group, and about 63% in the group administered with 3200 mg/kg body weight compared to that of the control group, thus showing that the occurrence of breast cancer is suppressed. When these results are expressed in an inhibitory ratio, those in the above described groups are about 32%, about 34%, about 38% and about 37%, respectively. *** in FIG. 5 indicates statistically significant differences relative to a control group, similar to those in FIGS. 1 to 4.

Figure 6:
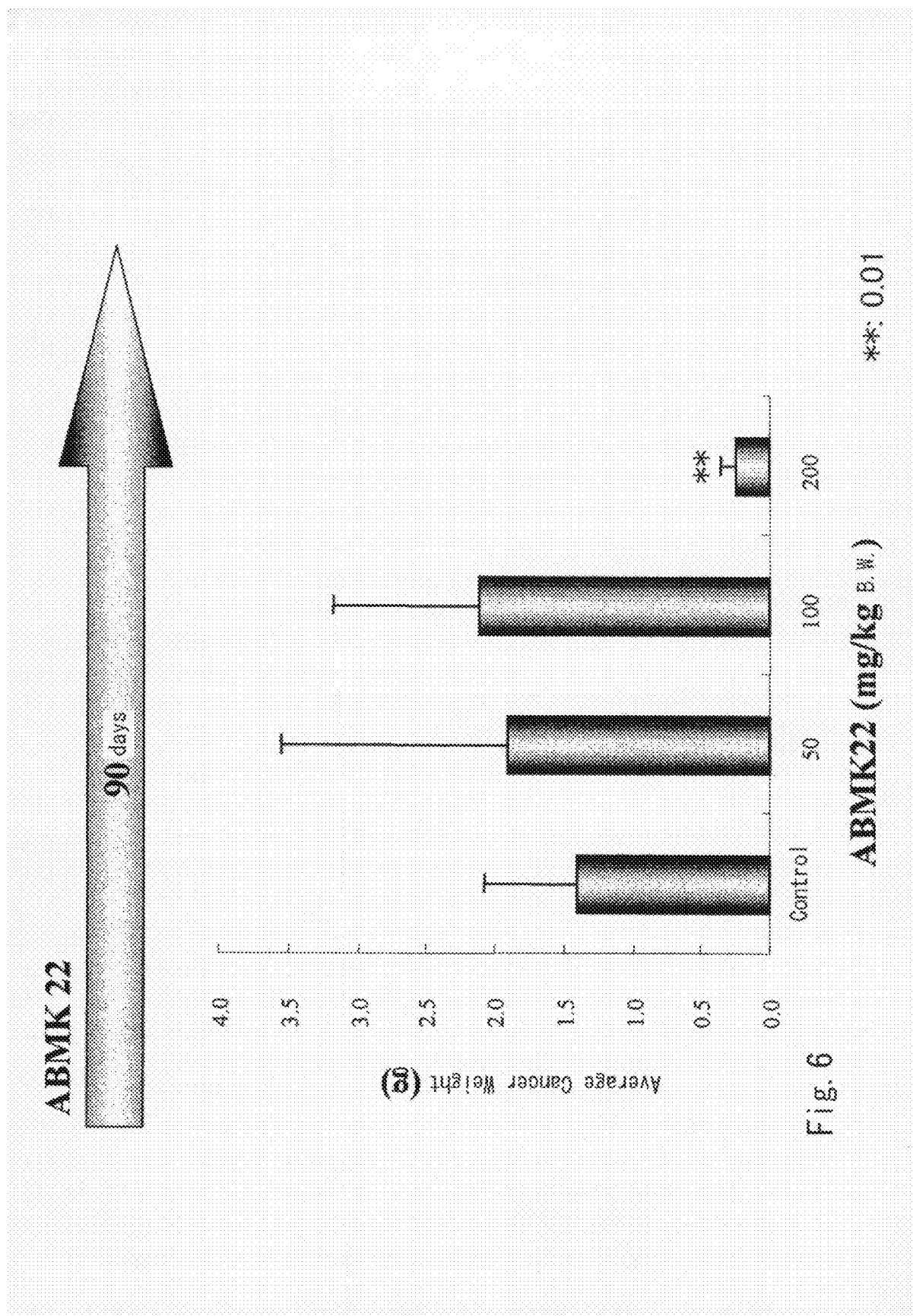
FIG. 6 shows effects of Kawariharatake extract (ABMK22) of the present invention which suppresses proliferation of breast cancer.

FIG. 6 indicates the average weight of breast cancer in each group in the test indicated in FIG. 4. From FIG. 6, the average weight of breast cancer tumor in rats of the group administered with 200 mg ABMK22/kg body weight is about 10%, relative to that of a control group and thus indicating a statistically significant difference.

Industrial Applicability

A drug material and a food material which prevent genesis of breast cancer and even proliferation of terminal breast cancer are provided.

The invention claimed is:
1. A method for suppressing breast cancer, comprising:
administering a composition to a subject having breast cancer, wherein the composition comprises a therapeu- tically effective amount of an *Agaricus blazei* Murill extract, and a pharmaceutically acceptable carrier.

2. A method for suppressing proliferation of terminal breast cancer, comprising:

administering a composition to a subject in need of suppressing proliferation of terminal breast cancer, wherein the composition comprises a therapeutically effective amount of an *Agaricus blazei* Murill extract, and a pharmaceutically acceptable carrier.

3. The method according to claim 1, wherein the extract is a chromatographic main elute fraction of 100 to 2000 molecular weight obtained by the steps of extracting a fruit body of *Agaricus blazei* Murill with hot water, dialyzing the resultant extract, and subjecting the thus obtained dialysis external fluid to chromatography.

4. The method according to claim 1, wherein the extract is a dialysis external fluid obtained by the steps of extracting a fruit body of *Agaricus blazei* Murill with hot water, adding ethanol to the resultant extract, thereby obtaining precipitates, dissolving the precipitates in water, and dialyzing the resultant solution.

5. The method according to claim 2, wherein the extract is a chromatographic main elute fraction of 100 to 2000 molecular weight obtained by the steps of extracting a fruit body of *Agaricus blazei* Murill with hot water, dialyzing the resultant extract, and subjecting the thus obtained dialysis external fluid to chromatography.

6. The method according to claim 2, wherein the extract is a dialysis external fluid obtained by the steps of extracting a fruit body of *Agaricus blazei* Murill with hot water, adding ethanol to the resultant extract, thereby obtaining precipitates, dissolving the precipitates in water, and dialyzing the resultant solution.

7. The method according to claim 1, wherein the breast cancer is induced by methyl-N-nitrosourea.

8. The method according to claim 2, wherein the breast cancer is induced by methyl-N-nitrosourea.

* * * * *